(12) United States Patent
Iwase

(10) Patent No.: US 9,763,323 B2
(45) Date of Patent: Sep. 12, 2017

(54) STRETCHABLE CIRCUIT BOARD

(71) Applicant: NIPPON MEKTRON, LTD., Tokyo (JP)

(72) Inventor: Masayuki Iwase, Tokyo (JP)

(73) Assignee: NIPPON MEKTRON, LTD., Tokyo (JP)

( * ) Notice: Subject to any disclaimer, the term of this patent is extended or adjusted under 35 U.S.C. 154(b) by 0 days.

(21) Appl. No.: 15/206,821

(22) Filed: Jul. 11, 2016

(65) Prior Publication Data

US 2017/0034907 A1   Feb. 2, 2017

(30) Foreign Application Priority Data

Jul. 30, 2015   (JP) .................................. 2015-151222

(51) Int. Cl.

| | |
|---|---|
| *H05K 1/00* | (2006.01) |
| *H05K 1/02* | (2006.01) |
| *A61B 5/11* | (2006.01) |
| *A61B 5/0402* | (2006.01) |
| *A61B 5/024* | (2006.01) |
| *A61B 5/021* | (2006.01) |
| *A61B 5/01* | (2006.01) |
| *A61B 5/00* | (2006.01) |

(52) U.S. Cl.
CPC ............. *H05K 1/0283* (2013.01); *A61B 5/01* (2013.01); *A61B 5/021* (2013.01); *A61B 5/024* (2013.01); *A61B 5/0402* (2013.01); *A61B 5/11* (2013.01); *A61B 5/6832* (2013.01); *A61B 2562/166* (2013.01)

(58) Field of Classification Search
CPC .. H05K 1/02; H05K 1/03; H05K 1/14; H05K 1/30; H05K 1/36; H05K 1/148; H05K 1/162; H05K 1/167; A61B 5/00; A61B 5/017; A61B 5/047; A61B 5/0492
USPC .......... 174/254, 250, 251; 29/830, 832, 825; 600/383, 384, 372, 393, 544; 361/752, 361/803; 439/86
See application file for complete search history.

(56) References Cited

U.S. PATENT DOCUMENTS

| | | | | |
|---|---|---|---|---|
| 4,967,038 A | * | 10/1990 | Gevins | A61B 5/0017 600/383 |
| 2005/0106907 A1 | * | 5/2005 | Yamada | G01R 1/0416 439/91 |

(Continued)

FOREIGN PATENT DOCUMENTS

| | | |
|---|---|---|
| JP | 2014-162124 A | 9/2014 |
| JP | 2014-236103 A | 12/2014 |

*Primary Examiner* — Xiaoliang Chen
(74) *Attorney, Agent, or Firm* — Westerman, Hattori, Daniels & Adrian, LLP

(57) ABSTRACT

Provided is a stretchable circuit board having a sheet-like stretchable base capable of stretching and contracting, a stretchable interconnect part formed on or above at least one major surface of the stretchable base, and an external terminal connected to the interconnect part; the stretchable circuit board has a reinforcing area having in-plane rigidity higher than that of the stretchable base, and a stretchable area which remains after excluding the reinforcing area; the interconnect part is formed across a boundary part between the reinforcing area and the stretchable area; and a sheet-like stretchable auxiliary member capable of stretching and contracting is provided to the boundary part having the interconnect part formed therein.

7 Claims, 10 Drawing Sheets

(56) References Cited

U.S. PATENT DOCUMENTS

| | | | |
|---|---|---|---|
| 2006/0148285 A1* | 7/2006 | Naoi | G01R 1/0735 |
| | | | 439/86 |
| 2008/0048698 A1* | 2/2008 | Amemiya | G01R 1/07342 |
| | | | 324/750.22 |
| 2015/0065840 A1* | 3/2015 | Bailey | A61B 5/6802 |
| | | | 600/384 |
| 2015/0141784 A1* | 5/2015 | Morun | G06F 3/015 |
| | | | 600/372 |
| 2015/0148641 A1* | 5/2015 | Morun | A61B 5/0492 |
| | | | 600/372 |
| 2015/0189753 A1* | 7/2015 | Goyal | H05K 1/0283 |
| | | | 361/803 |

* cited by examiner

F I G. 1
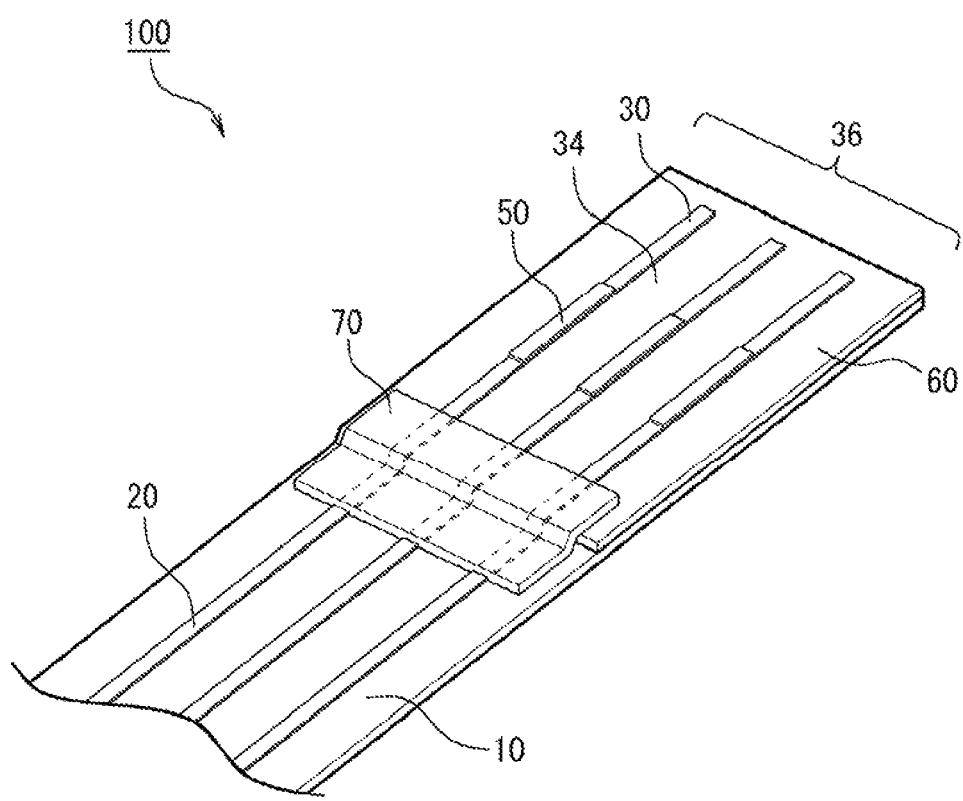

FIG. 3

| Overall elongation of stretchable circuit board before interconnect breaks | | Thickness of stretchable base | | |
|---|---|---|---|---|
| | | 10μm | 25μm | 40μm |
| Stretchable auxiliary member | Not used | 40% | 45% | 55% |
| | Used | 65%(40μm) | 65%(25μm) | 65%(10μm) |

F I G. 4
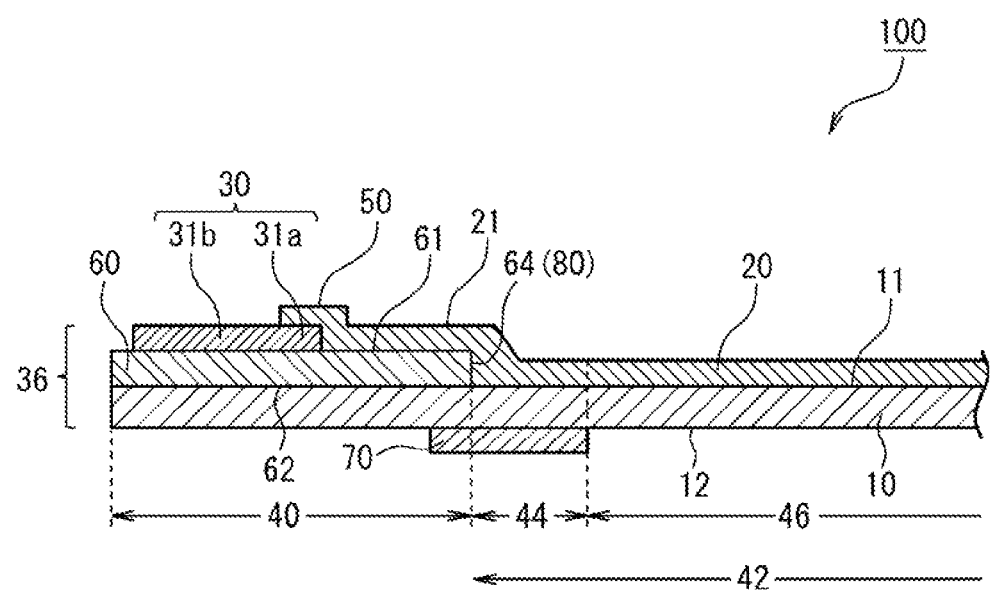

F I G. 7
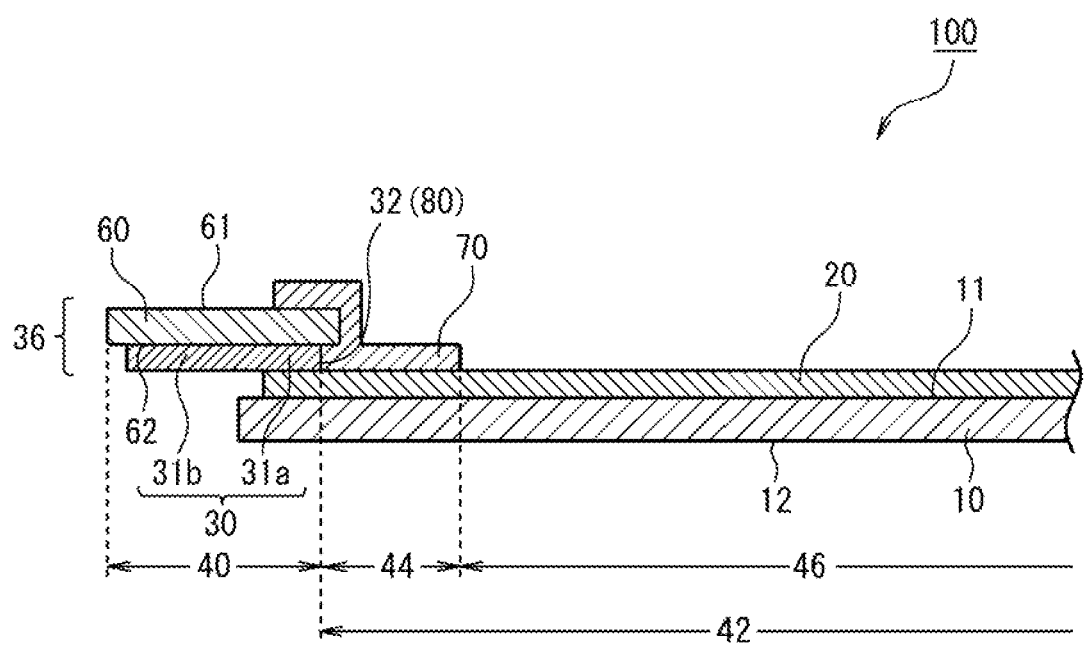

STRETCHABLE CIRCUIT BOARD

This application is based on Japanese patent application No. 2015-151222, filed on Jul. 30, 2015, the content of which is incorporated hereinto by reference.

BACKGROUND

Technical Field

This invention relates to a stretchable circuit board.

Related Art

There have been growing interests in biosensor and biological information monitor, in the recent market of wearable device and medical device. For example in the sport industry, trials have been made on precise quantification of physical motion, aiming at further enhancing physical abilities and skills of athletes. In some cases, wearable biosensors for sensing motion of living body have been applied. Meanwhile in the medical industry, trials have been made on sensing vital signs (biological information) including electrocardiogram, heart rate, blood pressure and body temperature, for the purpose of treatment and prevention of disease. For this purpose, the biological information monitor for detecting biological information has occasionally been applied. The biosensor and the biological information monitor are typically provided to clothes or fitting, so that sensing and monitoring are enabled when the clothes or fitting are worn.

Since, however, the clothes or fitting slightly shifts from the human body as the human body moves, so that the biosensor or the biological information monitor provided to the clothes or fitting would be misaligned from a target point of the living body, considerably lowering accuracy of sensing or monitoring.

The problems above may be suppressed by placing the biosensor or the biological information monitor directly onto the human body. In recent years, a technology called stretchable electronics, using an in-plane stretchable base and interconnects, has been investigated, and has come to propose a circuit board capable of stretching and contracting conforming to the motion of joint or the like of the human body.

Regarding this sort of stretchable circuit board, JP-A-2014-236103 describes a circuit board composed of a stretchable base, and an electro-conductive pattern containing an electro-conductive particle and an elastomer, thereby being made stretchable as a whole. Meanwhile, JP-A-2014-162124 describes a stretchable circuit board in which islands, formed by printing to give a film composed of a material having the Young's modulus larger than that of a stretchable base, are embedded in the base. Each island has a device mounted thereon, and the islands are mutually connected with stretchable interconnects. According to the description, with this configuration, the device and the interconnects which lie across boundaries between the islands and the base may be prevented from being broken, even if the stretchable base stretches or contracts.

[Patent Literature 1] JP-A-2014-236103
[Patent Literature 2] JP-A-2014-162124

In such stretchable circuit board described above, it is necessary to pay special attention to provide the interconnect part and other various constituents on the stretchable base, so as to tolerate the stretching and contraction. Since, however, in-plane rigidity or in-plane Young's modulus vary from constituent to constituent depending on their constitutive materials or thickness, so that the stretchable circuit board sometimes will not be uniform as a whole in terms of stretchability. In such case, stress during stretching and contraction may be concentrated locally, and thereby the interconnect part in such location may become more susceptible to breakage.

SUMMARY

This invention is conceived in consideration of the problems above, and is to provide a stretchable circuit board capable of relaxing local concentration of stress, and of preventing the interconnect part from being broken.

According to this invention, there is provided a stretchable circuit board which includes a sheet-like stretchable base capable of stretching and contracting, a stretchable interconnect part formed on or above at least one major surface of the stretchable base, and an external terminal connected to the interconnect part, the stretchable circuit board having a reinforcing area having in-plane rigidity higher than that of the stretchable base, and a stretchable area which remains after excluding the reinforcing area, the interconnect part being formed across a boundary part between the reinforcing area and the stretchable area, and a sheet-like stretchable auxiliary member, capable of stretching and contracting, being provided to the boundary part having the interconnect part formed therein.

According to this invention, since the stretchable auxiliary member is provided to the boundary part between the reinforcing area and the stretchable area, where stress is likely to concentrate due to difference in in-plane rigidity, so that the stretchable area will have formed therein an area having high in-plane rigidity (high-rigidity area), and an area having low in-plane rigidity (low-rigidity area). Accordingly, the stress concentration may be relaxed, and thereby the interconnect part formed at the boundary part may be prevented from being broken.

BRIEF DESCRIPTION OF THE DRAWINGS

The above and other objects, advantages and features of the present invention will be more apparent from the following description of certain preferred embodiments taken in conjunction with the accompanying drawings, in which:

FIG. 1 is a perspective view illustrating a stretchable circuit board of a first embodiment;

FIG. 3 is a table summarizing results a stretch test of the stretchable circuit board;

FIG. 4 is a vertical cross-section illustrating a stretchable circuit board of a second embodiment;

FIG. 7 is a vertical cross-section illustrating a stretchable circuit board of a fourth embodiment;

DETAILED DESCRIPTION

The invention will be now described herein with reference to illustrative embodiments. Those skilled in the art will recognize that many alternative embodiments can be accomplished using the teaching of the present invention and that the invention is not limited to the embodiments illustrated for explanatory purposes.

Embodiments of this invention will be explained below, referring to the attached drawings. In these drawings, all similar constituents will have the same reference signs, so as to properly omit the explanation.

In the embodiments below, the description will occasionally be made while specifying the vertical direction as illustrated, merely for the sake of convenience of explaining relative positional relation among the constituents, so that the vertical direction does not always coincide with the gravimetric vertical direction. "Plane" in the context of this specification does not require being a geometrically perfect plane, instead allowing recesses or projections formed thereon. "Sheet" in the context of this specification widely encompasses shaped articles with small thickness, such as film and membrane. In short, variation in the names of sheet, film and membrane by no means specify the individual thicknesses.

First Embodiment

Figure 2:
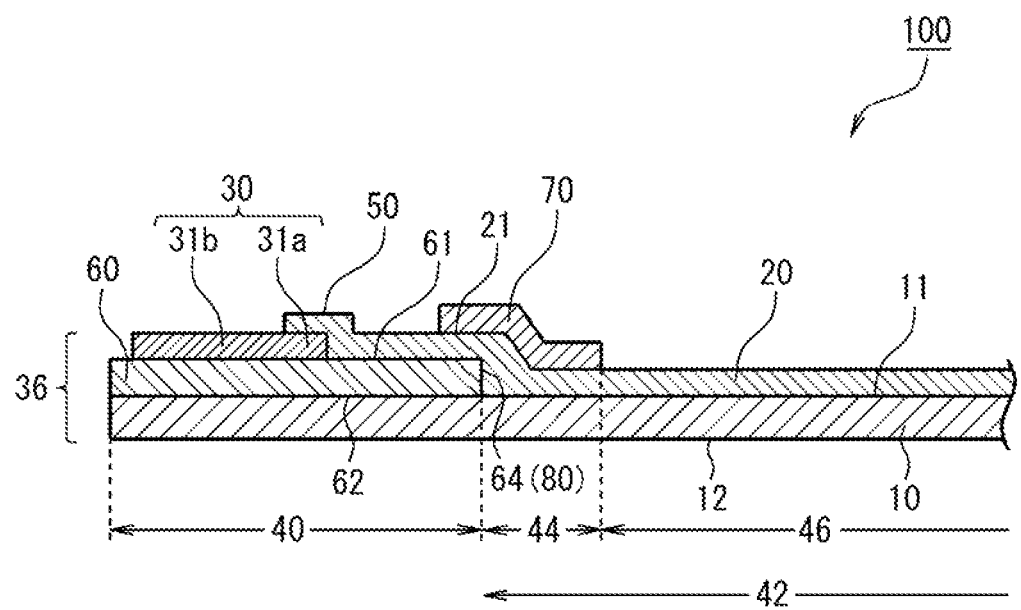
FIG. 2 is a vertical cross-section illustrating a stretchable circuit board of the first embodiment.

First, the first embodiment will be outlined referring to FIG. 1 to FIG. 3.

FIG. 1 is a perspective view illustrating a stretchable circuit board 100 of the first embodiment. FIG. 2 is a vertical cross-section illustrating the stretchable circuit board 100 of the first embodiment. FIG. 3 is a table summarizing results of stretch test of the stretchable circuit board 100.

Note that both of FIG. 1 and FIG. 2 illustrate only a part of side on which external terminal 30, provided so as to enable connection with a variety of external devices, is arranged, leaving the other part unillustrated.

The stretchable circuit board 100 has a sheet-like stretchable base 10 capable of stretching and contracting, a stretchable interconnect part 20 formed on or above at least the one major surface of the stretchable base 10, and an external terminal 30 connected to the interconnect part 20. The stretchable circuit board 100 also has a reinforcing area 40 having in-plane rigidity larger than that of the stretchable base 10, and a stretchable area 42 excluding the reinforcing area 40.

The interconnect part 20 is formed across a boundary part 80 between the reinforcing area 40 and the stretchable area 42.

A sheet-like stretchable auxiliary member capable of stretching and contracting 70 is provided at the boundary part 80 where the interconnect part 20 is formed.

As a result of such provision of the stretchable auxiliary member 70, the stretchable area 42 consequently has a high-rigidity area 44 having the stretchable auxiliary member 70 provided therein, and a low-rigidity area 46 which remains after excluding the high-rigidity area 44 from the stretchable area 42. As a matter of course, the high-rigidity area 44 has in-plane rigidity larger than that of the low-rigidity area 46, and the reinforcing area 40 has in-plane rigidity larger than those of the high-rigidity area 44 and the low-rigidity area 46.

In other words, the in-plane rigidity varies according to a decreasing order of "reinforcing area 40>high-rigidity area 44>low-rigidity area 46", showing a stepwise decrease in the in-plane rigidity as coming away from the reinforcing area 40. Accordingly, stress created by stretching and contraction of the stretchable circuit board 100 will be distributed rather than being concentrated to the boundary part 80, and thereby the interconnect part 20 may be prevented from being broken at the boundary part 80.

Next the stretchable circuit board 100 of this embodiment will be detailed.

The stretchable circuit board 100 has at least one external terminal 30 which is used for connection with a variety of external devices. Examples of the external devices include power unit, control board, and sensing part (not illustrated) which senses motion of living body, or biological information including electrocardiogram, heart rate, blood pressure, body temperature and so forth. In this way, the stretchable circuit board 100 may be used as a part of biosensor or biological information monitor. The sensing part may be mounted on the stretchable circuit board 100, and the stretchable circuit board 100 may have mounted thereon various electronic components such as resistor, capacitor and so forth.

The stretchable circuit board 100 may be used by placing it on the surface of human body, or by attaching it to robots, various devices, apparatuses and wearable goods. The stretchable circuit board 100 may have an adhesion layer (not illustrated) with which the stretchable base 10 is adhered to the surface of human body, robot or the like. The adhesion layer may be provided on the major surface of the stretchable base 10, specifically so as to cover the top face 11 of the portion having the interconnect part 20 formed thereon, or may be provided so as to cover the back face 12 which is opposite to the surface having the interconnect part 20 formed thereon.

Major constituents of the stretchable circuit board 100 include, as illustrated in FIG. 1, the stretchable base 10, the interconnect part 20, the external terminal 30, a connection part 50, a flexible film 60, and a stretchable auxiliary member 70.

The stretchable base 10 is a sheet-like member which can stretch and contract at least in one in-plane direction. Preferably, the stretchable base 10 is stretchable in two in-plane directions. The in-plane stretchability of the stretchable base 10 may be isotropic, or may be anisotropic characterized by different degrees of stretchability in a plurality of in-plane directions.

Preferred materials for composing the stretchable base 10 include, but not limited to, elastomer materials such as nitrile rubber, latex rubber, urethane-based elastomer and silicone-based elastomer. In particular, by employing a urethane-based elastomer sheet for medical use, an advanced safety will be obtained even when applied to the human skin.

Although not specifically limited, thickness of the stretchable base 10 is preferably 100 µm or thinner for example, from the viewpoint that a target of placement of the stretchable circuit board 100 (target surface) will not be inhibited from freely stretching and contracting. The thickness of the stretchable base 10 is more preferably 25 µm or thinner, and even more preferably 10 µm or thinner.

Note that the stretchable base 10 in this embodiment has a uniform thickness and Young's modulus over the entire range of the reinforcing area 40 and the stretchable area 42 of the stretchable circuit board 100, and in other words, the stretchable base 10 has a uniform in-plane rigidity over the entire range of the stretchable circuit board 100.

Maximum elongation of the stretchable base 10 is preferably 10% or larger, more preferably 50% or larger, even more preferably 100% or larger, and particularly 200% or larger. The stretchable base 10 composed of the above-described materials can even exhibit a maximum elongation of 300% or larger. Now the maximum elongation of the stretchable base 10 means a maximum value of elongation up to which the stretchable base 10 can elastically deform in one in-plane direction.

Note that "elongation" in this specification means the ratio of elongation in one in-plane direction under applied force, relative to the dimension under no external force (zero-elongation dimension). For example, 50% elongation means 1.5-fold elongation from the zero-elongation dimension, and 100% elongation means 2-fold elongation from the zero-elongation dimension.

On the back face 12 of the stretchable base 10 illustrated in FIG. 2, an adhesion layer and a separation sheet (not illustrated) may be provided. The adhesion layer may be formed by coating an adhesive agent. With this configuration, the stretchable circuit board 100 when used, will easily be placed on a target object (target surface) by peeling the separation sheet off and by bringing the adhesion layer into contact with the target.

The interconnect part 20 is provided to one surface of the stretchable base 10. The interconnect part 20 is configured to contain an electro-conductive material, and is therefore electro-conductive. The electro-conductive material is selectable from good conductors including silver, gold, platinum, carbon, copper aluminum, cobalt, nickel and alloys of these materials. The electro-conductive material may have any form of particles such as granule, powder, flake and so forth. The particle has an aspect ratio of 1 or larger and 100 or smaller typically, and in particular 1 or larger and 50 or smaller. The aspect ratio herein means the ratio of the maximum length and the minimum length of a three-dimensional article. By selecting an aspect ratio of 5 or larger and 20 or smaller for the particle composing the interconnect part 20, the interconnect part 20 may be suppressed from being largely varied in the resistivity, even if the stretchable circuit board 100 were stretched in the in-plane direction and the interconnect part 20 were deformed longitudinally.

It is further preferable for the interconnect part 20 to contain a resin binder, and thereby the interconnect part 20 may be suppressed from being broken due to stretching and contraction of the stretchable base 10. The resin binder is exemplified by, but not limited to, elastomer materials such as urethane resin binder and silicone rubber. The resin binder is preferably selected from those having small values of Young's modulus, so that the interconnect part 20, when given in a form of coated film, will have the Young's modulus equivalent to, or smaller than the Young's modulus of the stretchable base 10. Only a single species of the elastomer material may be used, or a plurality of elastomer materials may be used in combination.

The interconnect part 20 may be formed typically by printing, but not specifically limited thereto. That is, the interconnect part 20 in this embodiment is made of a printed pattern formed by coating a stretchable electro-conductive paste based on a printing process.

Methods of printing are exemplified by, but not specifically limited to, screen printing, ink jet printing, gravure printing and offset printing. Among them, screen printing is suitably used, from the viewpoints of fine resolution and stability of film thickness.

When the interconnect part 20 is formed by printing, it is preferable to prepare an electro-conductive paste containing the electro-conductive material and the resin binder described above, and then to subject it to printing. By using the stretchable electro-conductive paste mainly composed of silver or other metal particle for the interconnect part 20, an elongation of typically 50% or larger and 70% or smaller may be achieved, making it possible to form the interconnect with excellent stretchability.

The interconnect part 20 is configured to contain a plurality of interconnects. At least a portion of the interconnect part 20 is electrically connected to the external terminal 30 as described later.

Thickness and width of the interconnect part 20 may be determined, considering resistivity of the interconnect part 20 under no load, change in the resistivity when the stretchable base 10 is stretched, and dimensional restriction on the overall thickness and width of the stretchable circuit board 100. From the viewpoint of obtaining good stretchability well conforming to dimensional changes during stretching and contraction of the stretchable base 10, each interconnect part 20 is preferably 1000 μm wide or narrower, more preferably 500 μm wide or narrower, and even more preferably 200 μm wide or narrower. Each interconnect composing the interconnect part 20 preferably has a thickness of 25 μm or smaller, and more preferably 10 μm or larger and 15 μm or smaller.

An interconnect end part 21 of the interconnect part 20 and a base part 31$a$ of the external terminal 30 are overlapped to be connected mutually, to form the connection part 50. The interconnect part 20 and the external terminal 30 in this embodiment are typically, but not exclusively, formed on the same side with respect to the stretchable base 10 and the flexible film 60.

Note that the interconnect end part 21 denotes a partial area of the interconnect part 20, formed in the reinforcing area 40. The interconnect end part 21 and the interconnect part 20 are formed by printing, in an integrated manner using the same material. The interconnect end part 21 may have the width smile as, or larger than, or smaller than that of the residual portion of the interconnect part 20 formed on the stretchable base 10.

The external terminal 30 is an interface part which configures a plugging part 36 plugged in or unplugged from a connector (not illustrated) of an external device including power unit, control board and so forth, and is formed substantially so as not to stretch, or to be non-stretchable, in the in-plane direction. The plugging part 36 is configured to contain a plurality of external terminals 30. Between every adjacent external terminals 30, there is provided a space part 34, in which an insulating underlying layer (the flexible film 60 in this embodiment) exposes.

The external terminal 30 may have a thickness of, but not limited to, 10 μm or larger and 40 μm or smaller. By specifying the external terminal 30 to have a thickness of 10 μm or smaller, the external terminal 30 will have an improved durability against repetitive plugging and unplugging of the plugging part 36 to or from the external devices. Meanwhile by specifying the external terminal 30 to have a thickness of 40 μm or smaller, the plugging part 36 will be thinned and will remain flexible.

As illustrated in FIG. 1, the external terminal 30 in this embodiment is composed of a plurality of line patterns, and the plurality of line patterns are arranged in parallel while placing a space part 34 in between. The plurality of interconnects of the interconnect part 20 are connected correspondingly to the plurality of line patterns of the external terminal 30. By configuring the external terminal 30 as described above, it now becomes possible to make the external terminal 30 compatible to the connecter shape having been used widely for the interface of electronic board.

In this embodiment, the end side (left hand side of FIG. 2) of the external terminal 30 will be denoted as terminal end 31b, and the base side (right hand side of FIG. 2) will be denoted as terminal base 31a. The terminal base 31a and the terminal end 31b are the names of virtual sections of the external terminal 30, so that both areas need not be discriminable by an explicit boundary.

The connection part 50 is a portion where the external terminal 30 and the interconnect part 20 are connected. The connection part 50 in this embodiment is formed by superposing the interconnect end part 21 of the interconnect part 20, onto the terminal base 31a of the external terminal 30. Although this embodiment exemplifies the case where the interconnect part 20 and the external terminal 30 are formed so as to overlap with each other on the same side of an underlying layer (flexible film 60) to form the connection part 50, the configuration is not limited thereto. For example, the interconnect part 20 and the external terminal 30 may be formed respectively on the different sides of the flexible film 60, and may be connected by an interlayer connection part (not illustrated) via a through-hole.

The external terminal 30 of this embodiment contains a patterned metal film or foil formed in the reinforcing area 40. Specific examples of the metal material include copper, silver and aluminum. In this embodiment, a part of the reinforcing area 40, containing the external terminal 30, configures the plugging part 36. Method of forming the external terminal 30 is exemplified by, but not specifically limited to, etching and printing.

When the external terminal 30 in this embodiment is formed by using a metal film or foil, etching is preferably employed. When etching is employed, it will suffice to cover an underlying layer (the flexible film 60 in this embodiment) with a metal film, and to etch the film according to a pattern desired for the external terminal 30.

The external terminal 30 may further be plated on the top surface thereof with a metal such as nickel or gold. In short, the external terminal 30 may be configured using a single metal layer, or a plurality of metal layers. The external terminal 30 may alternatively be coated with an electroconductive nonmetallic material, as described later in the third embodiment.

The reinforcing area 40 is a local area whose in-plane rigidity is higher than that of the stretchable area 42, and at least higher than the in-plane rigidity of the stretchable base 10. Since, when the stretchable circuit board 100 is stretched in the in-plane direction, the reinforcing area 40 will only have a lowered stress as compared with the stretchable area 42, so that the external terminal 30 and the connection part 50 arranged within the reinforcing area 40 may be prevented from being broken or damaged. More specifically, in the connection part 50, the interconnect part 20 (interconnect end part 21) may be prevented from separating from the external terminal 30.

The Reinforcing area 40 may be formed by partially thickening the stretchable base 10, or by partially curing a material of the stretchable base 10, or by stacking thereon a film material different from the stretchable base 10. When partially curing a material of the stretchable base 10, it is possible for example that a UV curable rubber is used for the stretchable base 10, UV light is then irradiated covering the area where the external terminal 30 and the connection part 50 will be arranged therein, to thereby cure the stretchable base 10. The reinforcing area 40 may thus be formed.

The reinforcing area 40 in this embodiment is formed by stacking the flexible film 60, having the in-plane Young's modulus larger than that of the stretchable base 10, on or above the one major surface or the other major surface of the stretchable base 10. Moreover, the connection part 50 which connects the external terminal 30 and the interconnect part 20, the external terminal 30, and at least a part of the interconnect part 20 (interconnect end part 21) are provided in an area which overlaps the flexible film 60 and on one side (top face 11) of the stretchable base 10.

Although the flexible film 60 in this embodiment is stacked only on or above the one major surface (top face 11) of the stretchable base 10, the mode of stacking is not limited thereto. A pair of flexible films 60 may be stacked respectively on or above the one major surface (top face 11) and the other major surface (back face 12) of the stretchable base 10.

Note that the interconnect end part 21 is a local area of the interconnect part 20 which is formed in the reinforcing area 40. The interconnect part 20, and the interconnect end part 21 as a part of it, are formed by printing in an integrated manner using the same material. The width of the interconnect end part 21 may be equal to, or larger than, the width of the residual portion of the interconnect part 20 formed on the stretchable base 10.

Materials used for composing the flexible film 60 include, but not specifically limited to, synthetic resins having low sliding performance, high corrosion resistance and high strength, such as polyethylene terephthalate (PET), polyimide (PI), polyphenylene sulfide (PPS) or fluorine-containing resin. The top face 61 of the flexible film 60 has a frictional coefficient larger than those of the top face 11 and the back face 12 of the stretchable base 10.

At least a part of the flexible film 60 is stacked on or above the one major surface (top face 11) of the stretchable base 10. This embodiment specifically exemplifies, but not exclusively, the case where the entire portion of the flexible film 60 is stacked on the top face 11 of the stretchable base 10. For example, only a part of the flexible film 60 may alternatively be stacked on the stretchable base 10, leaving the other part protruded out from the stretchable base 10.

The external terminal 30, the interconnect part 20 and the connection part 50 in this embodiment are provided on the surface (top face 61) on one side of the flexible film 60.

According to this embodiment, it now becomes possible to configure the stretchable circuit board 100 as a so-called flexible printed circuit (FPC), or flexible flat cable (FFC), using the flexible film 60 as a base film, and patterning thereon the external terminal 30 by etching.

At least a part of the flexible film 60 is bonded directly to the one major surface or the other major surface of the stretchable base 10. More specifically, the flexible film 60 in this embodiment is bonded directly to the top face 11 of the stretchable base 10, over the entire portion of the back face 62. Now "the flexible film 60 is bonded directly to the stretchable base 10" means that the flexible film 60 and the stretchable base 10 are brought into direct contact, and then integrated by a bonding process such as heat pressing.

When a urethane-based elastomer sheet, fusible under heating, is used as the stretchable base 10, it may be integrated with the flexible film 60 to be bonded under heating, and may therefore be integrated in a stacked manner. By bonding the stretchable base 10 and the flexible film 60 by heat pressing, it now becomes possible to omit a bonding member to thereby simplify the bonding process. Another advantage is that the stretchable base 10 and the flexible film 60 will never bond with each other, unless otherwise heated and pressed, so that the workability will be improved even in the process of high precision alignment.

The flexible film 60 preferably has a thickness of 5 μm or larger and 100 μm or smaller, preferably 25 μm or smaller, and more preferably 12.5 μm or smaller. By specifying the thickness of the flexible film 60 within any of these ranges, the reinforcing area 40 may have a fully increased in-plane rigidity, and thereby the stretchable circuit board 100 may be thinned as a whole.

As illustrated in FIG. 2, in the stretchable circuit board 100 of this embodiment, the stretchable base 10 is laminated on the back face 62 of the flexible film 60. There is a difference in level at the boundary part 80 between the top face 61 of the flexible film 60 and the major surface (top face 11) of the stretchable base 10 on which the flexible film 60 is stacked. The difference in level is preferably 50 μm or smaller.

The interconnect part 20 is formed across the boundary part 80 so as to extend from the top face 61 of the flexible film 60 to the major surface (top face 11) of the stretchable base 10. The plurality of interconnects of the inter connect part 20 (interconnect end part 21) formed on the flexible film 60 are formed in parallel. In the stretchable area 42, the interconnect part 20 is formed into any desirable pattern.

Now, the stretchable interconnect part 20 is formed, as described above, typically by printing such as screen printing, by which an electro-conductive paste is coated patternwise. When the interconnect part 20 is formed by screen printing, by suppressing the difference in level at the boundary part 80 between the stretchable base 10 and the flexible film 60, any printing failure at that portion may be reduced to keep a continuity of the interconnect part 20. Accordingly, by suppressing the difference in level between the top face 11 of the stretchable base 10 and the top face 61 of the flexible film 60 to 50 μm or smaller, the interconnect part 20 may be formed across the boundary part 80 in a continuous and stable manner.

Such difference in level is equal to the thickness of the flexible film 60, when the stretchable base 10 and the flexible film 60 are directly bonded as in this embodiment. Alternatively when the flexible film 60 and the stretchable base 10 are bonded using an adhesive layer (not illustrated), the difference in level is equal to the total thickness of the flexible film 60 and the adhesive layer.

The boundary part 80 is defined as a line segment across which the interconnect part 20 lies, which is a part of the line segment which represents the boundary between the reinforcing area 40 and the stretchable area 42. The boundary part 80 in this embodiment agrees with the end face 64 of the flexible film 60.

The end face 64 (boundary part 80) of the flexible film 60, Illustrated as being upright in FIG. 2, may alternatively have a slope (not illustrated) formed typically by chamfering the end face 64 of the flexible film 60, so as to make the top face 61 decline towards the base side (rightward in FIG. 2). In this mode of embodiment, the boundary part 80 agrees with the end face on the base side of the slope (not illustrated). In this way, the interconnect part 20 which is formed across the boundary part 80 may be formed in a more stable manner, successfully preventing the interconnect part 20 from being broken.

The stretchable auxiliary member 70 is a sheet-like member stretchable at least in one in-plane direction. Preferably, the stretchable base 10 is stretchable in two in-plane directions. The stretchability of the stretchable base 10 may be isotropic, or may be anisotropic characterized by different degrees of stretchability in a plurality of in-plane directions. The stretchable auxiliary member 70 may be single-layered or multi-layered.

The stretchable auxiliary member 70 is a member which is bonded across the boundary part 80 between the reinforcing area 40 and the stretchable area 42 (high-rigidity area 44). In this embodiment, the stretchable auxiliary member 70 is formed on or above the one major surface of the stretchable base 10, and is bonded to a part of interconnect part 20 (interconnect end part 21) or to the top face 11 of the stretchable base 10.

The stretchable auxiliary member 70 and the stretchable base 10 are preferably composed of the same material. Preferred materials for composing the stretchable auxiliary member 70 include, but not limited to, nitrile rubber, latex rubber, urethane-based elastomer and silicone-based elastomer, all of which are same as those composing the stretchable base 10.

At least a part of the stretchable auxiliary member 70 is preferably bonded directly to the stretchable base 10. Now, "the stretchable auxiliary member 70 is bonded directly to the stretchable base 10" means that the stretchable auxiliary member 70 and the stretchable base 10 are directly brought into contact, and then integrated by a bonding process such as heat pressing. When the stretchable base 10 and the stretchable auxiliary member 70 are composed of urethane-based elastomer sheets, both are fusible under heating, so that both may be bonded under heating, and may be integrated in a stacked manner.

As described above, when the stretchable auxiliary member 70 and the stretchable base 10 are composed of the same material and are bonded directly, the bonded part between the stretchable auxiliary member 70 and the stretchable base 10 will have high strength, and correlation between the other element (for example, interconnect part 20) formed on the stretchable base 10 with the stretchable auxiliary member 70 will not be a causal factor of product failure. A similar effect may be obtained by bonding the stretchable auxiliary member 70, while placing in between an adhesive layer (not illustrated) which is again stretchable.

Results of a stretch test conducted on the stretchable circuit board 100 are summarized in FIG. 3. Note that the values of overall elongation summarized in FIG. 3 are representative values with a certain tolerance.

The stretch test was conducted to evaluate the overall elongation of the stretchable circuit board 100. In more detail, tensile load was applied to the stretchable circuit board 100, so as to make 5% increments of the overall elongation, and the overall elongation of the stretchable circuit board 100, when interconnect part 20 showed infinite resistivity, representing disconnection, was measured.

Both of the stretchable base 10 and the stretchable auxiliary member 70, which were contained in the stretchable circuit board 100 subjected to the stretch test, have an in-plane Young's modulus of 7.5 MPa.

From the results of the stretch test, the overall elongation was found to increase, when the stretchable auxiliary member 70 having a proper thickness was bonded to the stretchable base 10 of 10 μm, 25 μm or 40 μm thick, as compared with the case where the stretchable auxiliary member 70 was not used. Although the thickness of the stretchable auxiliary member 70 is not specifically limited, maximum improvement in durability against elongation before the interconnect part 20 breaks was observed when a 40 μm thick stretchable auxiliary member 70 was bonded to a 10 μm thick stretchable base 10; or when 25 μm thick stretchable auxiliary member 70 was bonded to a 25 μm thick stretchable base 10; or when a 10 μm thick stretchable auxiliary member 70 was bonded to a 40 μm thick stretchable base 10. It is therefore considered that the total thickness of the stretchable base 10 and the stretchable auxiliary member 70 is preferably 50 μm or around (40 μm or larger and 60 μm or smaller). Note that, for the case where the stretchable auxiliary member 70 has a multi-layered configuration, the total thickness of all layers represents the thickness of the stretchable auxiliary member 70, as described above. Note also that, for the case where the stretchable auxiliary member 70 and the stretchable base 10 are bonded using an adhesive layer described above, the thickness of the adhesive layer is contained in the thickness of the stretchable auxiliary member 70.

The result is largely attributable to that the low-rigidity area 46 was the first to stretch in the process of stretching the stretchable circuit board 100, and this was supposed to relax the stress concentrated into the boundary part 80 (boundary between the reinforcing area 40 and the high-rigidity area 44). In short, the stretchable circuit board 100 can relax local concentration of stress at the boundary part 80, and to prevent breakage of the interconnect part 20 formed across the boundary part 80.

Note that the stretch test is on the premise of using the stretchable base 10 and the stretchable auxiliary member 70 which are composed of the same material having an in-plane Young's modulus of 7.5 MPa. Accordingly, when the stretchable base 10 and the stretchable auxiliary member 70 are respectively composed of different materials, a preferred value of the total thickness of the stretchable base 10 and the stretchable auxiliary member 70 may vary.

Other embodiments of this invention will be described below, referring to the drawings, while properly avoiding redundant explanation already made in the first embodiment.

Second Embodiment

Next, the stretchable circuit board 100 of the second embodiment will be explained referring to FIG. 4. FIG. 4 is a vertical cross-section illustrating the stretchable circuit board 100 of the second embodiment.

The stretchable circuit board 100 of this embodiment is different from the first embodiment (see FIG. 2), in that the stretchable auxiliary member 70 is joined to the side (back face 12) different from the side (top face 11) having the interconnect part 20 and the external terminal 30 formed thereon.

Even When the stretchable auxiliary member 70 is joined to the back face 12 of the stretchable base 10 as shown above, rather than to the top face 11, the stretchable circuit board 100 can prevent the interconnect part 20 from being broken, so long as the position of joining falls on the boundary part 80 where the interconnect part 20 is formed.

Third Embodiment

Figure 5:
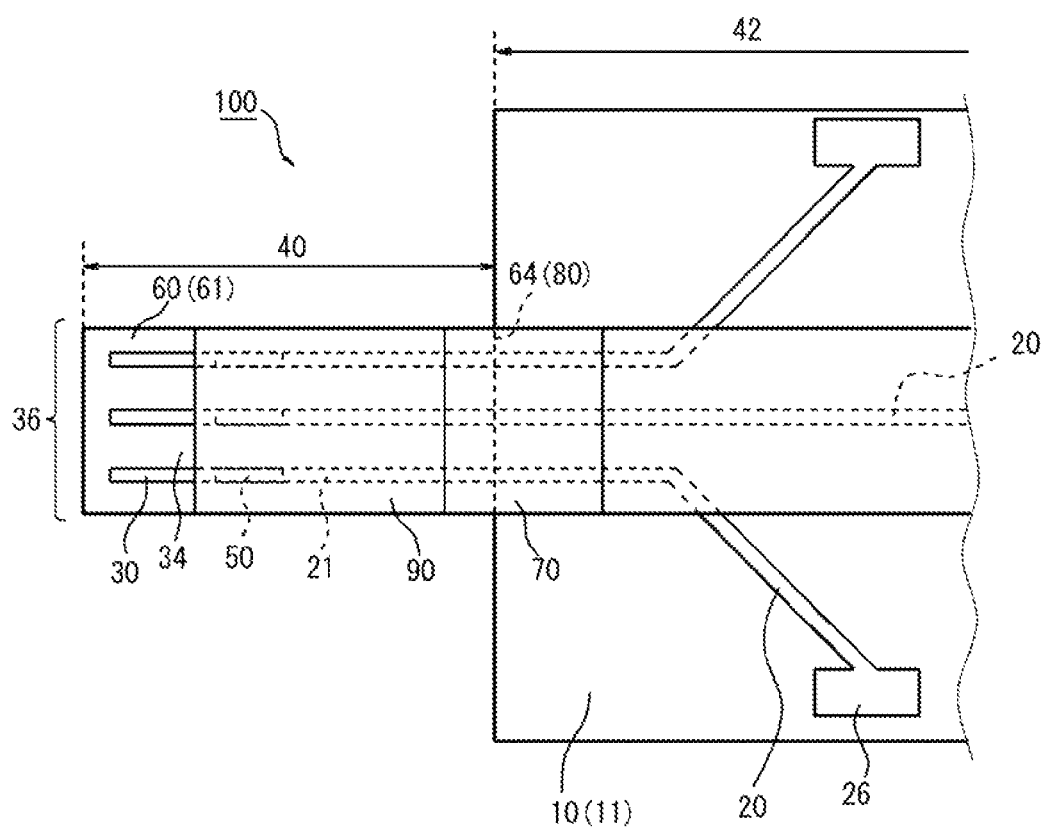
FIG. 5 is a schematic plan view illustrating a stretchable circuit board of a third embodiment.
Figure 6:
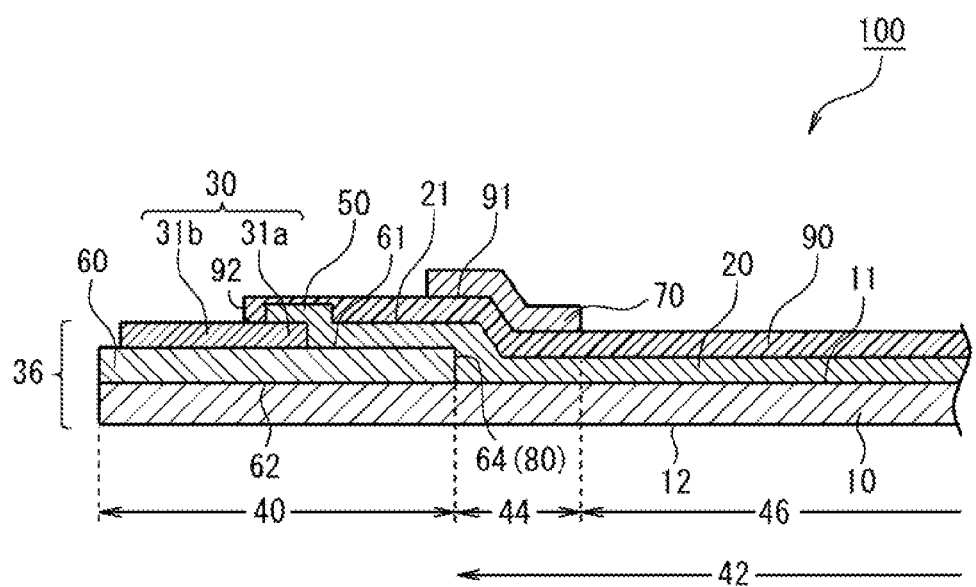
FIG. 6 is a vertical cross-section illustrating a stretchable circuit board of the third embodiment.

Next, the stretchable circuit board 100 of the third embodiment will be explained referring to FIG. 5 and FIG. 6. FIG. 5 is a schematic plan view illustrating the stretchable circuit board 100 of the third embodiment. FIG. 6 is a vertical cross-section illustrating the stretchable circuit board 100 of the third embodiment.

The stretchable circuit board 100 of this embodiment is different from the first embodiment (see FIG. 2) in that an electrode part 26 is formed as a part of the interconnect part 20, and that a protective layer 90 is provided so as to cover at least a part of the interconnect part 20 which remains after excluding the electrode part 26. It is different from the first embodiment again in that the stretchable auxiliary member 70 is bonded to the one major surface (top face 91) of the protective layer 90.

Since the interconnect part 20 is covered with the protective layer 90 in this way, it is now possible to prevent the interconnect part 20 from being damaged by accidental contact.

The electrode part 26 is a part of the interconnect part 20, and is formed to have a larger width than the residual portion. The electrode part 26 is, of course, electro-conductive since it is a part of the interconnect part 20. When the stretchable circuit board 100 is used as a biosensor or a biological information monitor, the electrode part 26 may serve as a portion brought into contact with the human body.

As illustrated in FIG. 5, the portion of the stretchable base 10 (stretchable area 42), having the electrode part 26 formed thereon, may be formed to have a larger width than the portion of the stretchable base 10 (plugging part 36) having the external terminal 30 formed thereon.

The protective layer 90 is a sheet-like layer which partially covers the interconnect part 20 formed in the stretchable area 42, and entirely covers the interconnect end part 21 formed in the reinforcing area 40. The protective layer 90 may be formed so as to cover the almost entire range of the top face 11 of the stretchable base 10, or may be formed selectively on a part of the top face 11 while covering the area where the interconnect part 20 is formed. With the protective layer 90, the stretchable base 10 as a whole can stretch in a relatively uniform manner when the stretchable circuit board 100 is stretched in the in-plane direction, and thereby the interconnect part 20 and the connection part 50 may be suppressed from being broken. Since the interconnect part 20 is held between the protective layer 90 and the stretchable base 10 in the thickness direction, the interconnect part 20 is positioned at around the center, in the thickness direction, of the stretchable circuit board 100. Accordingly, tensile stress and compressive stress, exerted on the interconnect part 20 when the stretchable circuit board 100 is bent in the direction normal to its surface, are canceled. The interconnect part 20 is thus protected.

The protective layer 90 is preferably composed of an insulating and stretchable material. An elastomer material, for example, may be used for the protective layer 90. Also usable is a resin material which is same as that composing the stretchable base 10 or the stretchable auxiliary member 70. In this way, the interconnect part 20 may be protected without degrading the stretchability of the stretchable circuit board 100. The protective layer 90 may be formed by coating an elastomer-based paste, onto the top face 61 of the flexible film 60 and the top face 11 of the stretchable base 10.

The thickness of the protective layer 90 is preferably, but not limited to, 100 μm or thinner from the viewpoint of avoiding inhibition on the stretchability of the stretchable circuit board 100, more preferably 50 μm or thinner, and even more preferably 30 μm or thinner. When the protective layer 90 is formed using the same resin material as the stretchable base 10 and the stretchable auxiliary member 70, the total thickness of the stretchable base 10, the stretchable auxiliary member 70 and the protective layer 90 is preferably 50 μm or around.

A part of the external terminal 30 (terminal base 31a), and the connection part 50 are covered with the protective layer 90. The residual portion (terminal end 31b) of the external terminal 30 is exposed out from the protective layer 90. In the process of forming a coating film of the protective layer 90 or in the process of bending the stretchable circuit board 100, stress may be concentrated on a front edge part 92 of the protective layer 90. In this case, the interconnect part 20 and the connection part 50 may be prevented from being broken, by arranging the edge part 92 of the protective layer 90 not on the weak connection part 50 or the interconnect part 20, but on the strong external terminal 30 typically composed of a metal film with high strength. The external terminal 30 may be composed not only of a metal film, but of a metal foil, and may be formed by a method of coating a nonstretchable electro-conductive paste containing silver, copper or carbon particle as the electro-conductive particle.

Fourth Embodiment

Next, the stretchable circuit board 100 of the fourth embodiment will be explained referring to FIG. 7. FIG. 7 is a vertical cross-section illustrating the stretchable circuit board 100 of the fourth embodiment.

The stretchable circuit board 100 of this embodiment is different from the first embodiment (see FIG. 2), in that the interconnect part 20 is laid along the top face 11 of the stretchable base 10, and the external terminal 30 and the flexible film 60 are formed on the surface of the interconnect part 20. This embodiment is again different from the first embodiment in that the boundary (boundary part 80) between the reinforcing area 40 and the stretchable area 42 is positioned at the end face 32 of the external terminal 30.

Since the interconnect part 20 is formed on the flat top face 11, so that coating based on a printing process of the interconnect part 20 will be easier than in the configuration of the first embodiment, and thereby the interconnect part 20 may be formed in a more stable manner at the boundary part 80.

Fifth Embodiment

Figure 8:
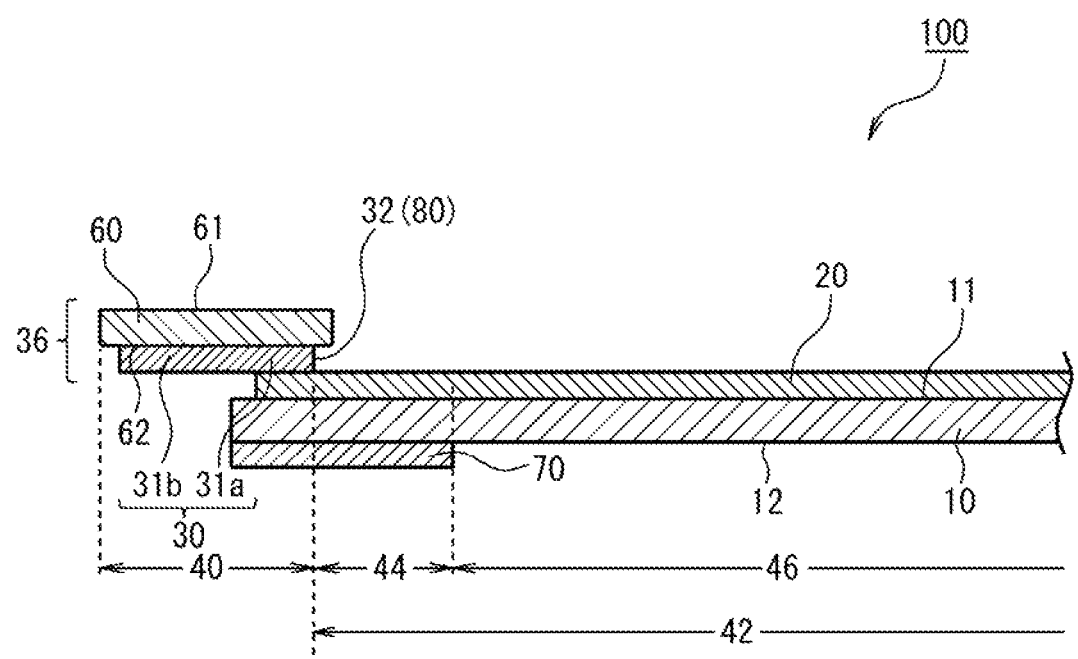
FIG. 8 is a vertical cross-section illustrating a stretchable circuit board of a fifth embodiment.

Next, the stretchable circuit board 100 of the fifth embodiment will be explained referring to FIG. 8. FIG. 8 is a vertical cross-section illustrating the stretchable circuit board 100 of the fifth embodiment.

The stretchable circuit board 100 of this embodiment is different from the second embodiment (see FIG. 4), in that the interconnect part 20 is laid along the top face 11 of the stretchable base 10, and that the external terminal 30 and the flexible film 60 are formed on the surface of the interconnect part 20. This embodiment is again different from the second embodiment, in that the boundary (boundary part 80) between the reinforcing area 40 and the stretchable area 42 is positioned at the end face 32 of the external terminal 30. Since the interconnect part 20 is formed in this way on the flat top face 11, so that coating based on a printing process of the interconnect part 20 will be easier than in the configuration of the second embodiment, and thereby the interconnect part 20 may be formed in a more stable manner at the boundary part 80.

The stretchable circuit board 100 of this embodiment is again different from the fourth embodiment (see FIG. 7), in that the stretchable auxiliary member 70 is bonded to the side (back face 12) different from the side (top face 11) on which the interconnect part 20 or the external terminal 30 are formed.

Sixth Embodiment

Figure 9:
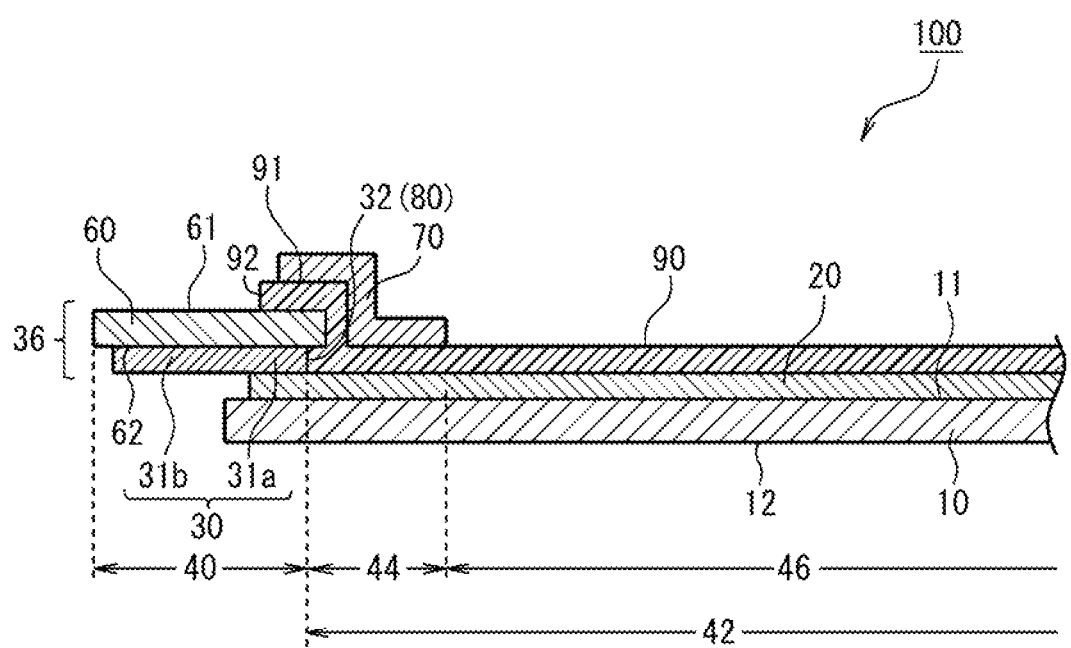
FIG. 9 is a vertical cross-section illustrating a stretchable circuit board of a sixth embodiment.

Next, the stretchable circuit board 100 of the sixth embodiment will be explained referring to FIG. 9. FIG. 9 is a vertical cross-section illustrating the stretchable circuit board 100 of the sixth embodiment.

The stretchable circuit board 100 of this embodiment is different from the third embodiment (see FIG. 6), in that the interconnect part 20 is formed along the top face 11 of the stretchable base 10, and the external terminal 30 and the flexible film 60 are formed on the surface of the interconnect part 20. This embodiment is again different from the third embodiment, in that the boundary (boundary part 80) between the reinforcing area 40 and the stretchable area 42 is positioned at the end face 32 of the external terminal 30. Since the interconnect part 20 is formed in this way on the flat top face 11, so that coating based on a printing process of the interconnect part 20 will be easier than in the configuration of the third embodiment, and thereby the interconnect part 20 may be formed in a more stable manner at the boundary part 80.

The stretchable circuit board 100 of this embodiment is again different from the fourth embodiment (see FIG. 7), in that it has the protective layer 90 which covers at least a part of the interconnect part 20, and in that the stretchable auxiliary member 70 is bonded to the one major surface (top face 91) of the protective layer 90. Since the interconnect part 20 is covered with the protective layer 90 in this way, it is now possible to prevent the interconnect part 20 from being damaged by accidental contact.

Seventh Embodiment

Figure 10:
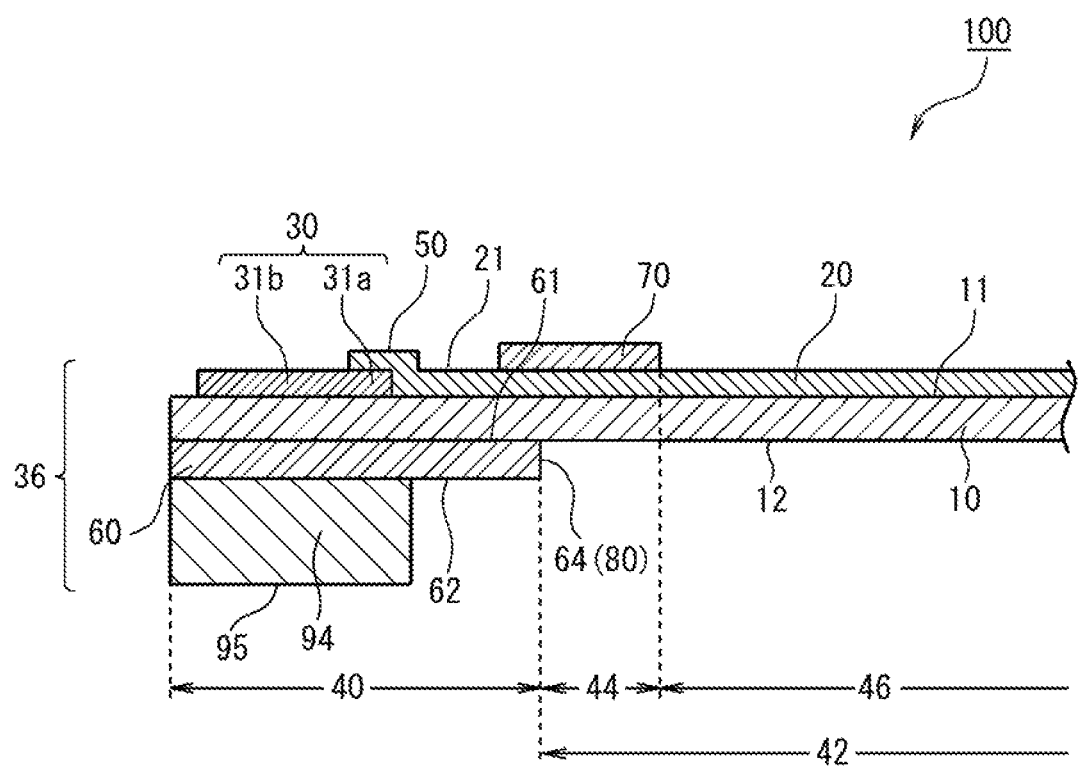
FIG. 10 is a vertical cross-section illustrating a stretchable circuit board of a seventh embodiment.

Next, the stretchable circuit board 100 of the seventh embodiment will be explained referring to FIG. 10. FIG. 10 is a vertical cross-section illustrating the stretchable circuit board 100 of the seventh embodiment.

The stretchable circuit board 100 of this embodiment is different from the first embodiment (see FIG. 2), in that the flexible film 60 is provided on the other side (back face 12) of the stretchable base 10, and in an area which overlaps at least a part of the external terminal 30.

The stretchable circuit board 100 of this embodiment is again different from the first embodiment, in that a reinforcement member 94 having the in-plane Young's modulus larger than that of the stretchable base 10 is provided on the other side of the stretchable base 10, and in an area which overlaps at least a part of the external terminal 30.

In more detail, the reinforcing area 40 is formed by stacking the flexible film 60 and the reinforcement member 94 on or above the other major surface (back face 12) of the stretchable base 10. The stretchable auxiliary member 70 is provided on or above the boundary part 80 between the reinforcing area 40 and the stretchable area 42, and is joined to either one of, or both of the one major surface (top face 11) and the other major surface (back face 12) of the stretchable base 10.

The reinforcement member 94, illustrated as provided below the flexible film 60 in FIG. 10, may alternatively be provided on or above the flexible film 60. The stretchable auxiliary member 70, illustrated as formed above the top face 11 of the stretchable base 10 in FIG. 10, may alternatively be formed on or above the back face 12 of the stretchable base 10, or may be formed on or above both of the top face 11 and the back face 12.

The reinforcement member 94 is provided, in a plan view of the stretchable circuit board 100, in an area which overlaps the external terminal 30, and on the side opposite to the external terminal 30, while placing the stretchable base 10 and the flexible film 60 in between. The footprint of the reinforcement member 94 is smaller than the footprint of the flexible film 60.

The reinforcement member 94 may be composed of, but not limited to, a synthetic resin such as polyethylene terephthalate or polyimide. The reinforcement member 94 is formed so that at least the back face 95 thereof will have a frictional coefficient smaller than that of the back face 12 of the stretchable base 10. The reinforcement member 94 may be formed using the same material as the flexible film 60.

Since the plugging part 36 becomes less deformable owing to the reinforcement member 94 provided thereto, so that workability in the process of inserting the plugging part 36 into a plugging-unplugging connector, accuracy of engagement, and reliability of connection may be improved. Since the thickness of the plugging part 36 is now freely adjustable owing to the provision of the reinforcement member 94, the plugging part 36 will have a high accuracy of plugging or unplugging, irrespective of whether a connector of an external device is plugging/unplugging type or fitting type.

Note that this invention is not interpreted solely by the above-described embodiments, but contains various modifications and improvements so long as the object of this invention may be achieved.

For example, although the embodiments showed the modes where a single plugging part 36 was formed on the stretchable circuit board 100, this invention is not limited to these modes. In particular, for the case where a sensing part which senses the biological information is not mounted on the stretchable circuit board 100, the stretchable circuit board 100 may additionally have the plugging part 36 used for connecting an external sensing unit, in addition to the plugging part 36 used for connecting the external power unit or control board.

Various constituents of the stretchable circuit board 100 of this invention are not always necessarily be independent entities, instead allowing typically that a plurality of constituents are formed as a single member, that a single constituent is formed by a plurality of members, that one constituent forms a part of other constituent, and that a part of one constituent overlaps a part of other constituent.

According to this invention, there is provided a stretchable circuit board capable of relaxing local stress concentration, and of preventing breakage of the interconnect part.

It is apparent that the present invention is not limited to the above embodiments, and may be modified and changed without departing from the scope and spirit of the invention.

These embodiments encompass the technical spirits below:

(1) A stretchable circuit board comprising a sheet-like stretchable base capable of stretching and contracting, a stretchable interconnect part formed on or above at least one major surface of the stretchable base, and an external terminal connected to the interconnect part,
the stretchable circuit board having a reinforcing area having in-plane rigidity higher than that of the stretchable base, and a stretchable area which remains after excluding the reinforcing area,
the interconnect part being formed across a boundary part between the reinforcing area and the stretchable area, and
a sheet-like stretchable auxiliary member, capable of stretching and contracting, being provided to the boundary part having the interconnect part formed therein.

(2) The stretchable circuit board according to (1),
wherein the stretchable area has, formed therein, a high-rigidity area having the stretchable auxiliary member provided therein, and a low-rigidity area of the stretchable area which remains after excluding the high-rigidity area, and
the high-rigidity area has in-plane rigidity larger than that of the low-rigidity area.

(3) The stretchable circuit board according to (1),
wherein the stretchable auxiliary member and the stretchable base are composed of the same material, and
at least a part of the stretchable auxiliary member is directly joined to the stretchable base.

(4) The stretchable circuit board according to (1),
wherein the reinforcing area is configured by stacking a flexible film, having the in-plane Young's modulus larger than that of the stretchable base, on or above the one major surface or the other major surface of the stretchable base, and
a connection part in which the external terminal and the Interconnect part, the external terminal, and at least a part of the interconnect part, are provided in an area which overlaps the flexible film and on one side of the stretchable base.

(5) The stretchable circuit board according to (4),
wherein a reinforcement member, having the in-plane Young's modulus larger than that of the stretchable base, is provided on the other side of the stretchable base and in an area which overlaps at least a part of the external terminal.

(6) The stretchable circuit board according to (5),
wherein the reinforcing area is formed on or above the other major surface of the stretchable base, by stacking the flexible film and the reinforcement member, and
the stretchable auxiliary member is provided at the boundary part between the reinforcing area and the stretchable area, and is joined either to the one or the other major surface, or to both major surfaces of the stretchable base.

(7) The stretchable circuit board according to (1),
wherein the interconnect part has, formed in a part thereof, an electrode part, and,
further comprising a protective layer which covers at least a part of the interconnect part which remains after excluding the electrode part.

What is claimed is:

1. A stretchable circuit board comprising a sheet-like stretchable base capable of stretching and contracting, a stretchable interconnect part formed on or above at least one major surface of the stretchable base, and an external terminal connected to the interconnect part,
the stretchable circuit board having a reinforcing area having in-plane rigidity higher than that of the stretchable base, and a stretchable area which remains after excluding the reinforcing area,
the interconnect part being formed across a boundary part between the reinforcing area and the stretchable area, and
a sheet-like stretchable auxiliary member, capable of stretching and contracting, being provided to the boundary part having the interconnect part formed therein.

2. The stretchable circuit board according to claim 1,
wherein the stretchable area has, formed therein, a high-rigidity area having the stretchable auxiliary member provided therein, and a low-rigidity area of the stretchable area which remains after excluding the high-rigidity area, and
the high-rigidity area has in-plane rigidity larger than that of the low-rigidity area.

3. The stretchable circuit board according to claim 1,
wherein the stretchable auxiliary member and the stretchable base are composed of the same material, and
at least a part of the stretchable auxiliary member is directly joined to the stretchable base.

4. The stretchable circuit board according to claim 1,
wherein the reinforcing area is configured by stacking a flexible film, having the in-plane Young's modulus larger than that of the stretchable base, on or above the one major surface or the other major surface of the stretchable base, and a connection part in which the external terminal and the interconnect part, the external terminal, and at least a part of the interconnect part, are provided in an area which overlaps the flexible film and on one side of the stretchable base.

5. The stretchable circuit board according to claim 4, wherein a reinforcement member, having the in-plane Young's modulus larger than that of the stretchable base, is provided on the other side of the stretchable base and in an area which overlaps at least a part of the external terminal.

6. The stretchable circuit board according to claim 5, wherein the reinforcing area is formed on or above the other major surface of the stretchable base, by stacking the flexible film and the reinforcement member, and the stretchable auxiliary member is provided at the boundary part between the reinforcing area and the stretchable area, and is joined to either one of, or both of the one major surface and the other major surface of the stretchable base.

7. The stretchable circuit board according to claim 1, wherein the interconnect part has, formed in a part thereof, an electrode part, and, further comprising a protective layer which covers at least a part of the interconnect part which remains after excluding the electrode part.

* * * * *